US00PP18937P2

(12) United States Plant Patent
Sheehan

(10) Patent No.: US PP18,937 P2
(45) Date of Patent: Jun. 17, 2008

(54) GRAPEVINE DENOMINATED 'SHEEGENE-1'

(50) Latin Name: *Vitis vinifera*
Varietal Denomination: Sheegene-1

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 8 days.

(21) Appl. No.: 11/594,045

(22) Filed: Nov. 6, 2006

(51) Int. Cl.
*A01H 5/00* (2006.01)

(52) U.S. Cl. ..... Plt./206
(58) Field of Classification Search ..... Plt./206
See application file for complete search history.

(56) References Cited

U.S. PATENT DOCUMENTS

PP4,787 P * 11/1981 Olmo et al. ..... Plt./205

* cited by examiner

*Primary Examiner*—Wendy C. Haas
(74) *Attorney, Agent, or Firm*—Worrel & Worrel

(57) ABSTRACT

A new and distinct variety of grapevine which is somewhat remotely similar to the 'Crimson' grapevine (not patented), but from which it is distinguished by producing fruit which are mature for harvesting and shipment approximately two (2) to three (3) weeks prior to the fruit produced by the 'Crimson' grapevine (not patented) and wherein the fruit are seedless berries which are juicy with an excellent flavor, red skin coloration and a moderately firm and tough skin. The berries of the new variety are borne on strong, woody stems which are well adapted to commercial handling.

1 Drawing Sheet

Latin name of the genus and species of the plant claimed: *Vitis vinifera.*

BACKGROUND OF THE NEW VARIETY

The present invention relates to a new and distinct variety of grapevine, which will hereinafter be denominated varietally as the 'Sheegene-1' grapevine, and, more particularly, to a grapevine which produces grapes, which are mature for commercial harvesting and shipment approximately September 16$^{th}$ through September 30$^{th}$ in the San Joaquin Valley of central California. The present variety produces large, seedless berries with a sweet flavor and red coloration over the entire berry.

The discovery or hybridization and development of new plant varieties is a process which requires arduous efforts over many years by skilled experts. This expertise requires not only acute powers of observation, but also the capability of dependably asexually reproducing the selected new variety. The asexually reproduced plants must be observed over many years of growth in order to confirm that they are identical to the parent. Such monitoring of the plants is also required to confirm that they possess the attributes desired for commercial development.

These assiduous efforts are required for all new plant varieties which are considered for commercial development, but are particularly important in the case of grapevines. Grapevines are, in addition to the more common maladies, subject to diseases, pests, climatic variations and may be adversely affected by a lack of proper husbandry. This latter condition may result from the fact that grapevines normally require a number of steps throughout the year in order to produce a commercially viable crop. Where all of these steps are not taken or they are inadequately performed, the crop will suffer.

For these reasons and others, a great many new varieties of grapevines have been developed throughout history which possess those attributes which are considered improvements over previously known varieties. Such development of new varieties has accelerated as the commercial value of grapes rapidly increased. Accordingly, the characteristics of grapes which are appealing to the consumer are sought after in the development of new varieties. Such characteristics for the fruit as size, color, flavor, whether seeded or seedless, shipping and handling quality and the like are sought after.

The new variety of grapevine of the present invention has been found to possess a promising combination of these characteristics for commercial development, as will hereinafter be set forth in greater detail.

ORIGIN AND ASEXUAL REPRODUCTION OF THE NEW VARIETY

The new variety is the result of hybridization of the 'Princess' grapevine (not patented), the pollen parent, with the 'Red Globe' grapevine (U.S. Plant Pat. No. 4,787), the seed parent, in 2000. The new variety was first planted in 2001. The first flowering was produced in 2003. The new variety was then asexually propagated in the spring of 2004 and grafted on to Thompson 2A (unpatented), virus free, rootstock. Two grapevines of the new variety were planted in a variety lot block of *Vitis vinifera* located near the town of McFarland in the San Joaquin Valley of central California, United States of America. The asexually reproduced grapevines of the subject invention first produced fruit in 2005. The inventor has observed the grapevine of the subject invention and has confirmed that the asexually reproduced grapevines are identical to the parent grapevine in all respects.

SUMMARY OF THE NEW VARIETY

The grapevine of the present invention is characterized by producing a large, dark red, seedless grape which has very good external coloration and excellent flavor and is mature for commercial harvesting and shipment approximately September 16th through September 30th in the San Joaquin Valley of central California. The new variety of grapevine is most closely similar to the 'Crimson' grapevine (not patented), but is distinguishable therefrom by the aforementioned ripening date, which is two (2) to three (3) weeks before that of the 'Crimson' grapevine (not patented), and by producing grapes with more overall red coloration and more flavor.

BRIEF DESCRIPTION OF THE DRAWING

The drawing is a color photograph which displays representative portions of the new variety of grapevine hereof in the upper portion showing three mature leaves positioned from left to right to show the upper surfaces of the first two leaves and the third positioned to show the lower surface thereof; in the center of the photograph a mature cluster of berries; in the right center of the photograph secondary growth clusters; immediately below the mature clusters of berries, berries are shown which are sectioned longitudinally and in cross section displaying the flesh thereof; in the bottom portion of the photograph, younger leaves are positioned to show the upper and lower surfaces thereof; and on the far left of the photograph is mature cane, all of the new variety of grapevine of the present invention.

DETAILED DESCRIPTION

Referring more specifically to the botanical details of this new and distinct variety of grapevine, the following has been observed under the ecological conditions prevailing at the vineyard of origin which is located near the town of McFarland in the San Joaquin Valley of central California, United States of America. All major color code designations are by reference to the *Dictionary of Color,* By Maerz and Paul, First Edition, 1930. Common color names are also occasionally employed.

Generally:

*Size.*—Large for 3-year-old vine.
*Vigor.*—Very good.
*Chilling Requirements.*—Normal for grapes in the San Joaquin Valley of central California.
*Productive capacity.*—Very good.
*Regularity of bearing.*—Regular.

Trunk:

*Size.*—Large, 16.3 cm (6.3 inches) circumference, measured 45.72 cm (18 inches) above ground.
*Surface texture.*—Shaggy, rough.
*Color.*—Inner Bark — Pl.17 E9 Kaffa, Hamptead Brown.
*Canes.*—Moderate to large in length. Length — 36.83 cm (14.5 inches) long.
*Mature canes.*—Color — Pl.7 L6 India Red, Aralian Red and Red Robbin.
*Nodes.*—Number — 6 on mature canes.
*Length between nodes.*—9.22 cm (3.63 inches).
*Lenticels.*—Numbers — Few, 5 to 7 between nodes. Size — Variable, 0.41 cm (0.16 inch) to 1.3 cm (0.51 inch).
*Shoots.*—Size — Medium. Length — Variable. Shape — Somewhat stocky. Contour — Somewhat drooping.
*Tendrils.*—Number — Very few between nodes. Length — Near nodes — Variable, 6.48 cm (2.55 inches) to 18.01 cm (7.09 inches). Location — At nodes. Form — Bifurcated and in some cases trifurcated. Texture — Woody.
*Buds.*—Shape — Slightly pointed. Size — Length — 1.32 cm (0.52 inch). Width — 0.81 cm (0.32 inch). Fruitfulness — Very good.

Branches:

*Size.*—Medium, 8.51 cm (3.35 inches) measured 35 cm (13.78 inches) from trunk.
*Surface texture.*—Slightly rough.
*Color.*—One year or older wood — Pl.6 J10 Spanish Cedar. Immature branches — Pl.19 L5 Cosse gr.
*Surface texture.*—Immature growth — Smooth.
*Lenticels.*—Numbers — 0.

Leaves:

*Size.*—Generally — Medium.
*Density.*—Dense.
*Size.*—Mature Leaf — Average Length — 13.56 cm (5.34 inches). Average Width — 16 cm (6.3 inches).
*Form.*—Pentagonal.
*Texture.*—Upper Surface — Smooth. Lower Surface — Smooth.
*Color.— Upwardly Disposed Surface — Pl.*22 L7 Art gr. Downwardly Disposed Surface — Pl.20 G6 Pea Green. Leaf Vein — Pl.20 K6 Piquant gr.
*Marginal form.*—Generally — Involute.
*Leaf vein.*—Thickness — 0.2 cm (0.08 inch).
*Leaf margin.*—Slightly undulate.
*Glands.*—None.
*Petiole.*—Size — Medium. Length — Average 0.76 cm (0.3 inch). Thickness — Average 0.2 cm (0.08 inch). Color — Pl.20 K6 Piquant gr.
*Petiole sinus.*—Form — V-shape.
*Stem glands.*—Absent.
*Stipules.*—Size — Large. Length — 0.41 cm (0.16 inch). Width — 0.41 cm (0.16 inch). Color — Pl.56 J12 Port Wine.
*Lobes.*—Normally 3, sometimes 4.
*Teeth.*—Size — Length — 0.51 cm (0.2 inch). Width — 0.51 cm (0.2 inch). Number — 3 between lobes. Shape — Convex.

Inflorescence:

*Size.*—15.01 cm (5.91 inches).
*Number borne per spur.*—1 to 2.
*Number borne per vine.*—Many.

Flowers:

*Flower buds.*—Size — Small. Surface Texture — Glabrous.
*Flowers.*—Generally — Heavy. Date of Bloom — May 15, 2006. Date of Full Bloom — May 18, 2006. Size — average 0.51 cm (0.2 inch).
*Petals.*—Color — Pl.7 H6 Peony Burmese Ruby +. Size — Small, less than 0.06 cm (0.02 inch).
*Pistils.*—Color — Pl.17 L3 Endive.
*Date of visible berries set.*—May 19, 2006.
*Size.*—Generally — 0.18 cm (0.07 inch).

Fruit

Maturity when described: Ripe for commercial harvesting and shipment approximately September 15th through September 30th in the San Joaquin Valley of central California in a normal year.

*Solids.*—19.6.
*Acid.*—0.37.
*Sugar/Acid Ratio. — Well balanced,* 53.7.
*Juice PH.*—4.24.
*Seeds.*—None.

*Capstem.*—Pedicel — Size — Length — 0.2 cm (0.08 inch). Width — 0.51 cm (0.2 inch). Color — Pl.22 L4 Cerro.

*Berry.*—Weight — Approximately 11.34 grams (0.4 oz.).

*Juice color.*—Pl.4 G1 Livid V.

Size:

*Cluster.*—Size — Generally — Medium to large. Average Length — 29.97 cm (11.8 inches). Average Width — 13 cm (5.12 inches). Weight — 718.956 grams (25.36 oz.). Compactness — Compact. Form — Conical.

*Stem.*—Generally — Size — Average 0.81 cm (0.32 inch). Caliper — Average 0.2 cm (0.08 inch).

*Berry.*—Size — Generally — Large. Form — Ovate to obtuse ovate. Number — Approximately 155 berries per bunch. Size — Average Dimension in longitudinal axis — 2.84 cm (1.11 inches) to 3 cm (1.18 inches). Average Dimension in axis transverse to longitudinal axis — 2.01 cm (0.79 inch).

Skin:

*Thickness.*—Medium.

*Texture.*—Tough.

*Tendency to crack.*—None observed.

*Color.*—Blush color — Pl.54 L12 De'Medici. Ground Color — None.

*Pulp*—Clear.

*Lenticels.*—None.

Flesh:

*Flesh color.*—From clear to Pl.5 L5 Cardinal.

*Juice production.*—Very good.

*Flavor.*—Excellent.

*Aroma.*—Mild.

*Texture.*—Semi tough.

*Ripening.*—Even.

*Eating quality.*—Excellent.

Use: Fresh market — Table grape.

Keeping quality: Very good.

Resistance to disease: Unknown.

Harvesting and shipment: Mid-September through early October.

Shipping and handling qualities: Very good.

Although the new variety of grapevine possesses the described characteristics noted above as a result of the growing conditions prevailing in the central San Joaquin Valley of California, it is to be understood that variations of the usual magnitude and characteristics incident to changes in growing conditions, irrigation, fertilization, pruning, pest control, climatic variations and the like are to be expected.

Having this described and illustrated my new variety of grapevine, what I claim as new and desired to be secured by Plant Letters Patent is:

1. A new and distinct variety of grapevine substantially as illustrated and described which is somewhat remotely similar to the 'Crimson' grapevine (not patented), but from which it is distinguished by producing fruit which are mature for commercial harvesting and shipment approximately September $15^{th}$ through September $30^{th}$, or about two (2) to three (3) weeks before the 'Crimson' grapevine (not patented), in the San Joaquin Valley of central California, and which produces large grapes with more overall red coloration and more flavor.

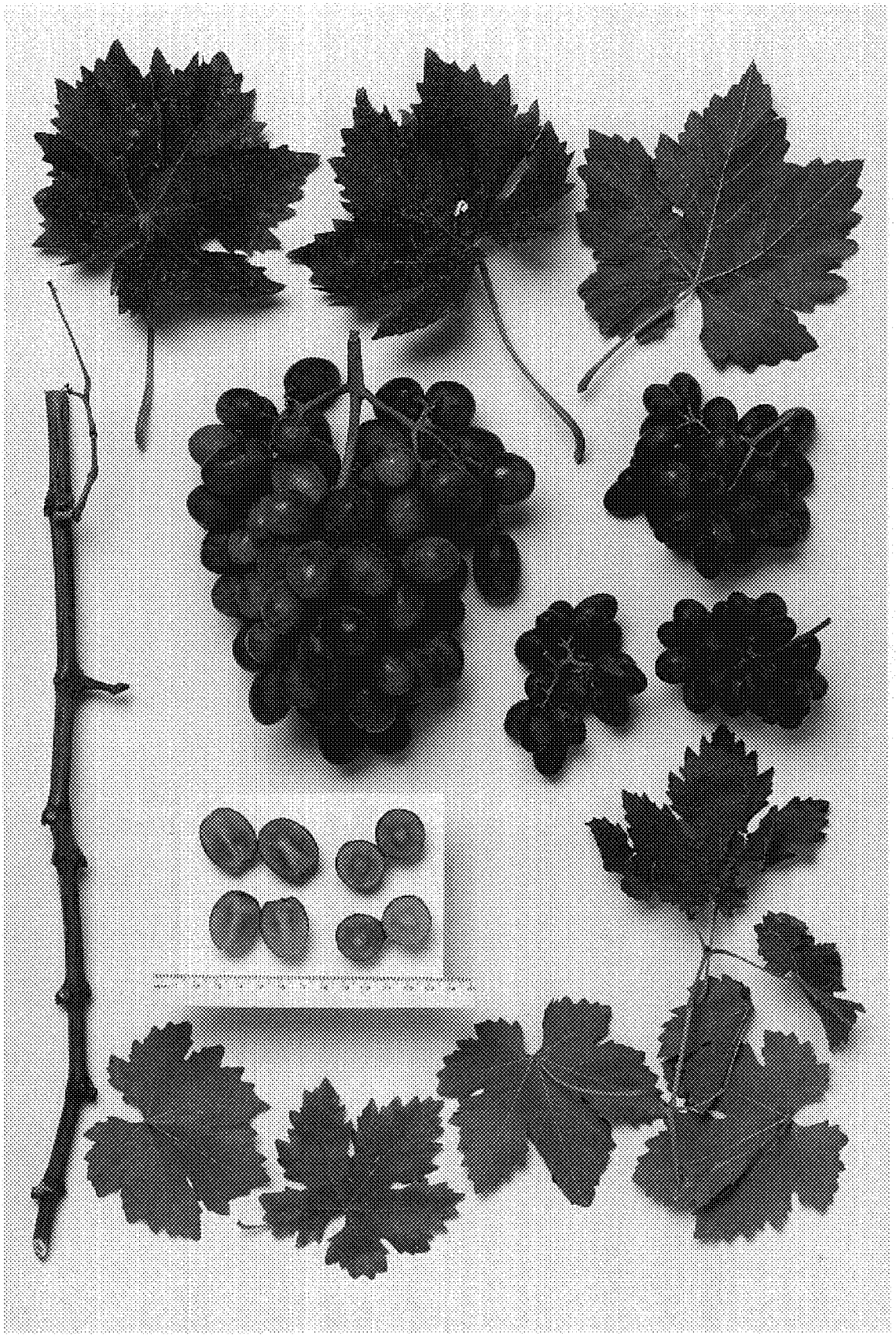

* * * * *